US00PP23984P2

(12) United States Plant Patent
Ladan

(10) Patent No.: US PP23,984 P2
(45) Date of Patent: Oct. 15, 2013

(54) ***ESCALLONIA* PLANT NAMED 'LADES'**

(50) Latin Name: *Escallonia laevis*
Varietal Denomination: Lades

(76) Inventor: Ludovic Ladan, Meillars (FR)

( * ) Notice: Subject to any disclaimer, the term of this patent is extended or adjusted under 35 U.S.C. 154(b) by 117 days.

(21) Appl. No.: 13/385,219

(22) Filed: Feb. 7, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Penny J. Aguirre

(57) ABSTRACT

A new cultivar of *Escallonia* named 'Lades' that is characterized by its compact, mounded plant habit, its glossy foliage that is medium green when young and dark green when mature, and its panicles of numerous medium pink tubular flowers.

2 Drawing Sheets

Botanical classification: *Escallonia laevis.*
Variety denomination: 'Lades'.

BACKGROUND OF THE INVENTION

The present invention relates to a new and distinct cultivar of *Escallonia laevis* and will be referred to hereafter by its cultivar name, 'Lades'. 'Lades' is a new cultivar of *Escallonia* shrub grown for use as a landscape plant.

The inventor discovered 'Lades' as a naturally-occurring whole plant mutation in a garden in Meillars, France in summer of 2003. The parentage of 'Lades' is unknown.

Asexual reproduction of the new cultivar was first accomplished by the Inventor using softwood stem cuttings in summer of 2003 in Meillars, France. The characteristics of 'Lades' have been determined to be stable and are reproduced true to type in successive generations.

SUMMARY OF THE INVENTION

The following traits have been repeatedly observed and represent the characteristics of the new cultivar as grown outdoors in trial beds and in containers in Meillars, France. These attributes in combination distinguish 'Lades' as a unique cultivar of *Escallonia.*

1. 'Lades' exhibits a compact, mounded plant habit.
2. 'Lades' exhibits glossy foliage, medium green when young and dark green when mature.
3. 'Lades' exhibits panicles of medium pink tubular flowers.
4. 'Lades' exhibits numerous flowers per inflorescence.

'Lades' can be compared to the following two cultivars of *Escallonia laevis*, 'Gold Ellen' (not patented) and 'Gold Brian' (syn. 'Hopley's Gold', not patented). 'Gold Ellen' differs from 'Lades' in having darker pink flowers, lighter green foliage, being taller in height (less compact), and in being less floriferous. 'Gold Brian' differs from 'Lades' in having darker pink flowers, new foliage that is yellow in color, and in being slightly taller in height. 'Lades' can also be compared to cultivars of *Escallonia* of hybrid origin, 'Jamie' (U.S. Plant Pat. No. 20,180), 'Red Dream' (not patented) and 'C. F. Ball' (not patented). 'Jamie' differs from 'Lades' in having a prostrate growth habit. 'Red Dream' differs from 'Lades' in having a dwarf plant habit and flowers that are more red in color. 'C. F. Ball' differs from 'Lades' in having flowers that are more red in color, in being much taller in height, and in having smaller leaves.

BRIEF DESCRIPTION OF THE DRAWING

The accompanying colored photographs illustrate the overall appearance and distinct characteristics of a 2-year-old plant of new *Escallonia* as grown outdoors in a garden in Meillars, France.

The photograph in FIG. 1 provides a side view of 'Lades' in bloom and illustrates its plant habit.

Figure 1:
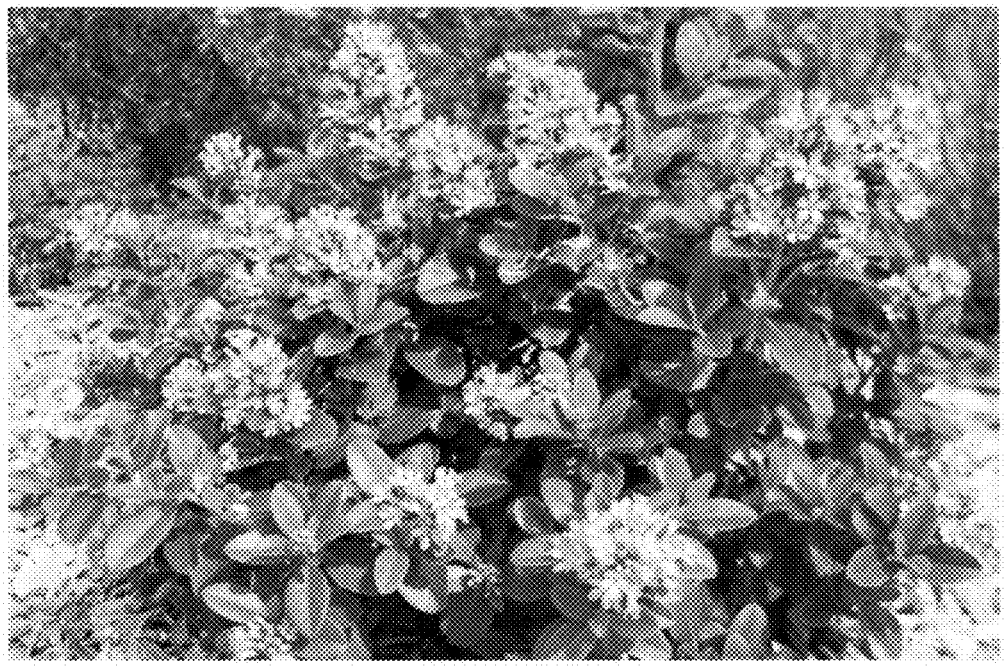
Figure 2:
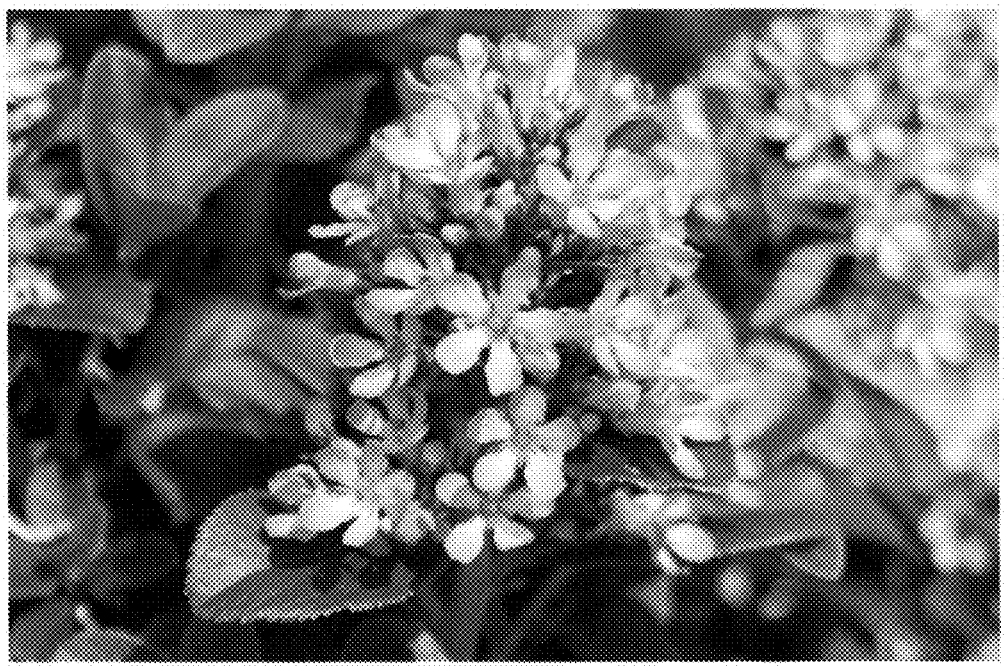

The photograph in FIG. 2 provides a close-up view of an inflorescence of 'Lades'.

The colors in the photographs are as close as possible with the digital photography techniques utilized and the color values cited in the detailed botanical description which accurately describe the colors of the new *Escallonia.*

DETAILED BOTANICAL DESCRIPTION

The following is a detailed description of 1 year-old plants of the new cultivar as grown outdoors in 2-liter containers in The Netherlands. The plants were grown with an average day temperature of 12° to 30° C. and an average night temperature of 8° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms in late spring to midsummer in The Netherlands.

*Plant type.*—Perennial, evergreen shrub.

*Plant habit.*—Compact with a mounded plant habit.

*Height and spread.*—Reaches about 16.1 cm in height and 29 cm in spread in a 2-liter container, reaches about 1.2 m in height and 60 cm in width when fully mature in the landscape.

*Hardiness.*—Cold hardy to U.S.D.A. Zone 7.
*Diseases resistance.*—Not more susceptible to pests and diseases than other *Escallonia.*
*Root description.*—Fibrous.
*Propagation.*—Softwood stem cuttings.
*Growth rate.*—Moderate.

Stem description:
*Stem shape.*—Round.
*Stem strength.*—Strong.
*Stem color.*—Young; 145B to 145D, mature; N199D.
*Stem size.*—Lateral branches average 11.8 cm in length and 3 mm in diameter.
*Stem surface.*—Slightly glossy, with shallow axial ribs, moderately covered with small glands, average length; 0.5 mm, color; 202A.
*Stem aspect.*—Outward to upright, angle varying between 30° and 65°.
*Internode length.*—Average of 8 mm.
*Branching.*—Average of 8 lateral branches as grown in a 2-liter container.

Foliage description:
*Leaf shape.*—Elliptic.
*Leaf division.*—Simple.
*Leaf base.*—Attenuate.
*Leaf apex.*—Obtuse.
*Leaf fragrance.*—None.
*Leaf venation.*—Pinnate, 144C in color on upper surface, 146C in color on lower surface.
*Leaf margins.*—Finely serrate.
*Leaf arrangement.*—Alternate.
*Leaf attachment.*—Petiolate.
*Leaf surface.*—Smooth, moderately glossy on upper and lower surface.
*Leaf size.*—Average of 3.7 cm in length and 2.1 cm in width.
*Leaf color.*—Young upper surface; 144B, mature upper surface; N137A, young lower surface; 144B, mature lower surface; 146B.
*Stipules.*—Not present.
*Petioles.*—Average of 5 mm in length and 1.5 mm in diameter, upper surface; 144B, lower surface; 144C, surface smooth and very slightly glossy.

Inflorescence description:
*Inflorescence type.*—Terminal panicle.
*Lastingness of inflorescence.*—Individual flowers last about 5 days.
*Inflorescence size.*—Average of 5.0 cm in length and 4.8 cm in width.
*Flower size.*—Average of 1.1 cm in length, 1.4 cm in diameter and 1.2 cm in depth.
*Flower fragrance.*—None detected.
*Flower number.*—Average of 55 per inflorescence, one inflorescence per stem.
*Flower aspect.*—Outward to upright.
*Flower bud.*—Narrow obovate in shape, an average of 9 mm in length and 3 mm in width, color; N57D with sepal portion 144B.
*Flower form.*—Tubular, single.
*Petals.*—Average of 5, rotate, smooth and dull on upper and lower surface, un-fused, narrow obovate in shape, obtuse apex, narrow cuneate base, entire margin, 1.5 cm in length; 4 mm in width, color; upper surface when opening; N57D, base 56D, fading to 61C, lower surface when opening; N57D, fading to 61D, upper surface when fully opened; N57D, base 56D, fading to 61C, lower surface when fully opened; 55B, base 56D, fading to 61D.
*Sepals.*—5, fused into a campanulate shaped calyx, broad elliptic, fused into a campanulate shape, broad acuminate apex, fused base, entire margins, 6 mm in length, 3 mm in width, upper and lower surface is slightly glossy, upper surface moderately covered with small glands about 0.5 mm in height and 202A in color, color; 144B on upper surface and 144A on lower surface.
*Peduncle size.*—Round in shape, strong, held vertical on top of lateral branch, an average of 4.3 cm in length and 2 mm in diameter, 143A in color, slightly glossy surface with shallow axial ribs moderately covered with glands about 0.5 mm in height and 202A in color.
*Pedicel.*—Round in shape, held at about a 45° degree angle to peduncle, 4 mm in length and 1 mm in diameter, smooth and dull surface, moderately strong, 144A in color.

Reproductive organs:
*Gynoecium.*—1 pistil, about 9 mm in length, club-shaped stigma 143A in color, style about 8 mm in length and 145B in color.
*Androcoecium.*—5 stamens, filament is about 8 cm in length and NN155C in color, ovary 143A in color.
*Fruit/seeds.*—No fruit set (or seeds) were observed.

It is claimed:

1. A new and distinct cultivar of *Escallonia* plant named 'Lades' as herein illustrated and described.

* * * * *